United States Patent [19]

Leerschool et al.

[11] Patent Number: 4,591,644
[45] Date of Patent: May 27, 1986

[54] METHOD AND INSTALLATION FOR THE PREPARATION OF MELAMINE

[75] Inventors: Joseph F. M. Leerschool, Beek; Hubert J. Dols, Geleen, both of Netherlands

[73] Assignee: Stamicarbon B.V., Geleen, Netherlands

[21] Appl. No.: 628,602

[22] Filed: Jul. 6, 1984

[30] Foreign Application Priority Data

Dec. 21, 1983 [NL] Netherlands ................. 8304381

[51] Int. Cl.$^4$ ............................................. C07D 251/60
[52] U.S. Cl. ................................... 544/201; 544/200
[58] Field of Search .............................. 544/201, 200

[56] References Cited

U.S. PATENT DOCUMENTS 3,598,818 8/1971 Krekels ............................ 544/200
3,711,479 1/1973 Verstegen et al. ............... 544/203

FOREIGN PATENT DOCUMENTS 1608236 8/1976 Fed. Rep. of Germany .
1153107 5/1969 United Kingdom .
1333544 10/1973 United Kingdom .

OTHER PUBLICATIONS

"Corrosion and Corrosion Prevention in Stainless Steel Urea Plants", Chemical Age of India, vol. 26, No. 4, Apr. 1975; De Jonge et al., pp. 249-260.
Hamilton, J. W., Ferralium—The Alternative to Mechanically Weak Austenitic Stainless Steel, Process Engineering, Jan. 1972.
Brochure of Langley Alloys Ltd., entitled "Langley Corrosion Resistance" undated Background Art.
Brochure of Langley Alloys Ltd., (in German) entitled "Ferralium Alloy 255" undated Background Art.
Chemical Abstracts, vol. 80, 1974, p. 168, Abstract No. 29599q.
Chemical Abstracts, vol. 91, 1979, p. 178, Abstract No. 91:7990k.

*Primary Examiner*—John M. Ford
*Attorney, Agent, or Firm*—Cushman, Darby & Cushman

[57] ABSTRACT

An improved method for the preparation of melamine from urea and/or thermal decomposition products thereof. The melamine reactor synthesis effluent is quenched by means of an aqueous medium to form an aqueous solution or suspension of melamine which is processed and solid product melamine removed therefrom. At least a portion of the melamine solution or suspension is processed in equipment having surfaces exposed to such solution or suspension fabricated from a stainless steel with a ferritic austenitic duplex structure containing, by weight 20 to 30 percent by weight chromium, 1 to 10 percent by weight nickel from 0 to about 10 percent manganese, such that the sum of the nickel plus one-half of the manganese content is within the range of between 4 and 10 percent, 1 to 5 percent by weight molybdenum, 0 to 3 percent by weight copper, not more than 0.1 percent by weight carbon and for the rest iron.

3 Claims, No Drawings

METHOD AND INSTALLATION FOR THE PREPARATION OF MELAMINE

BACKGROUND OF THE INVENTION

This invention relates to an improvement in a method for the preparation of melamine by the conversion of urea and/or thermal decomposition products thereof wherein the melamine synthesis reactor effluent is cooled with an aqueous medium to form a aqueous melamine solution or suspension wherefrom solid product melamine is eventually recovered. The melamine synthesis reactor effluent additionally contains ammonia and carbon dioxide which are also in part dissolved in the aqueous medium used to quench the melamine effluent. Such a method for the preparation of melamine is known from, for instance, U.S. Pat. No. 3,711,479.

A number of difficulties arise in the preparation of melamine, particularly in the processing of the above-noted melamine solutions or suspensions which additionally contain ammonium carbamate. Aqueous solutions of ammonia and carbon dioxide (hereinafter referred to as aqueous ammonium carbamate solutions) are known to have a very corrosive effect on several types of stainless steel, particularly at elevated temperatures.

The present invention specifically relates to an improved process for the preparation of melamine utilizing as a material of construction a particular chromium-nickel stainless steel alloy having a ferritic-austenitic structure, in order to combat the severe corrosion and errosion conditions uniquely encountered in the preparation of melamine.

Extensive research has been conducted into the suitability of various alloys as materials of construction for surfaces coming into contact with aqueous ammonium carbamate solutions. This research, however, has particularly centered around ammonium carbamate solutions formed in connection with the preparation of urea. For example, a survey of corrosion rates of several chromium-nickel steels subjected to aqueous ammonium carbamate solutions in urea synthesis processes is set forth in an article by R. deJonge et al entitled "Corrosion and Corrosion Prevention in Stainless Steel Urea Plants", Chem. Age. of India 26 pp. 249–260 (1975).

Chromium-nickel alloys having a duplex ferritic-austenitic structure of the type utilized herein have been known and utilized in chemical processing for a number of years. See, for example, German Auslegeschrift No. 1,608,236. Moreover, such alloys have been suggested as a material of construction for apparatus utilized in preparation of urea. Thus, British Pat. No. 1,153,107 describes a method for preparing urea wherein one or more surfaces that come into contact with ammonium carbamate consist of a steel alloy having at least 20 percent by weight chromium, 1-7 percent by weight nickel, and 1-4 percent by weight molybdenum.

The use of ferritic-austenitic steels containing 25 percent by weight chromium, from 1 to 6 percent by weight nickel, and from 1 to 3 percent by weight molybdenum are also noted in British Pat. No. 1,333,544 as being suitable for use in urea synthesis processes. Even with this material, however, it is recommended that passivating oxygen be utilized. This reference then goes on to teach that the disadvantages inherent in the use of passivating oxygen can be avoided in urea processing by utilizing on surfaces coming into contact with ammonium-carbamate a nickel-free ferritic steel consisting essentially of at least 25 percent by weight of chromium, and from 0 to 3 percent by weight molybdenum, with a combined carbon plus nitrogen content of not more than 0.035 percent by weight. However, such nickel-free chromium-iron alloys have the disadvantage that special measures must be taken to preserve their corrosion resistance when they are welded, as is necessary in the fabrication of processing equipment.

Although ammonium carbamate is believed to be the major cause of equipment corrosion in both the preparation of melamine and the preparation of urea, it has been found that a material suitable for the preparation of urea is not, as a matter of course, suitable for the preparation of melamine. Conversly, those materials found suitable for the preparation of melamine are not necessarily also suitable for the preparation of urea. Extensive research has been conducted in an attempt to explain why this is so, but without success.

A clear distinction between the two processes lies in the fact that in the preparation of urea it is possible to reduce corrosion by adding a minor amount of oxygen to passivate the stainless steel. In general, it is essential when using chromium-nickel steels that oxygen should be added. It is not feasible, however, to add oxygen in the preparation of melamine as the presence of oxygen interferes with the preparation of melamine. Nevertheless, this difference does not account for the difference in corrosion performance found with various of alloys when used as a material of construction for the preparation of urea, on one hand, and for the preparation of melamine, on the other.

An object of the present invention is to provide a method for the preparation of melamine, as described above, wherein the corrosion of the processing equipment caused by aqueous solutions of ammonium carbamate, as well as errosion due to the presence of solid matter in the liquid streams, is reduced to a minimum.

BRIEF DESCRIPTION OF THE INVENTION

In accordance with the present invention, at least a portion of the melamine solution or suspension is processed in equipment having surfaces which are exposed thereto fabricated from a stainless steel having a ferritic-austenitic duplex structure containing, by weight from about 20 to 30 percent chromium, 1 to 10 percent nickel, from 0 to about 10 percent manganese, such that the sum of the nickel plus one-half of the manganese content is within the range of between 4 and 10 percent, 1 to 5 percent molybdenum, 0 to 3 percent copper, and not more than 0.1 percent carbon, with the remainder being iron and not more than about 5 percent by weight impurities and/or other additives, relative to the total weight of the stainless steel.

Surprisingly, this specific alloy has been found to exhibit superior properties under the very diverse conditions that occur in the processing of aqueous ammonium carbamate solutions formed in the preparation and processing of melamine without the addition of passivating oxygen. This alloy has been found particularly resistant to the combined corrosive-errosive conditions present upon the condensation of ammonia and carbon dioxide out of the gas phase, and upon contact with ammonium carbamate in the liquid phase, containing solid particles.

The alloy used in the process of this invention may contain up to 3.0 percent by weight copper, more preferably between about 1 and 2.5 percent, but it is not necessary that any copper be present. This alloy may also contain minor amounts of contaminants or impurities such as silicon, sulphur, phosphorus and trace amounts of anyone of the eluents of the remainder of periodic table of elements. In general, the total amount of contaminant will not be more than about 2 percent by weight. In addition, the alloy may also contain some nitrogen, for example between 0.05 and 0.5 percent.

In order to further improve the resistance of the stainless steel to intercrystalline corrosion, a minor amount of additives, for instance between about 0.2 and 1.0 percent by weight titanium, niobium, or a combination of niobium and tantalum, may be incorporated in the alloy.

An essential aspect of the improved method in accordance with this invention is that the stainless steel alloy must have a ferritic austenitic structure, that is, a duplex structure. The exact structure of the alloy is dependent upon the composition of the chromium-nickel steel, and assuming rapid cooling from higher temperatures (such as with welding or casting), can be derived from a Schaeffler diagram such as is published in Colombier, Hochmann, Aciers inoxydables aciers refractaires Paris, 1965, p. 24, or from calculations such as those given in Peckner & Bernstein, Handbook of Stainless Steels (1977), pp. 4–29 and 11-3. In determining this structure, however, allowance should be made for the fact that, with rolled products, the structure depends also on the thermal history of the material.

The weight ratio of ferrite to austenite in the alloys used in accordance with this invention should in general lie between 95-5 and 5-95. Beyond these limits, the structure can no longer be referred to as being "duplex". This ratio should preferably lie between about 25-75 and 75-25, even more preferably at approximately 50-50.

In the method according to the present invention, the above-noted specific materials of construction are most advantageously applied in that equipment which is subjected to high flow velocities, solid-containing liquid suspensions, condensation, or a combination thereof. It is preferable not to add oxygen or an oxygen compound so as not to adversely influence the melamine preparation.

The melamine preparation to which this invention is applicable may be carried out by various known methods, such as those described in U.S. Pat. Nos. 3,711,479 and 3,598,818. Preferably, the melamine is prepared by a catalytic conversion of urea and/or its thermal decomposition products at atmospheric or an elevated pressure at a temperature of between about 300° and 450° C. However, the invention may also advantageously be applied to non-catalytic processes wherein the melamine reactor synthesis effluent is directly quenched into an aqueous medium.

In general, the pressure of the catalytic reaction will not be chosen higher than about 25 bar inasmuch as little advantage is obtained with catalytic processes at higher pressures. At higher pressures, it is preferable to convert urea to melamine without a catalyst, in which case the melamine-containing melt thus obtained may be cooled, possibly after a decrease of pressure, with water or an aqueous solution. However, a low-pressure process is preferred.

In a low-pressure melamine process, the melamine reactor reacting gas mixture obtained, containing melamine vapor, is quenched by direct contact and cooling with water or an aqueous solution, forming a solution or suspension of melamine in an ammonium carbamate solution. Where an aqueous solution is used for cooling or quenching the synthesis reactor effluent, this aqueous solution may conveniently be mother liquor recirculated from a subsequent processing step. The melamine solution or suspension thus obtained may be subjected to a number of processing steps, including concentration, stripping, heating, dissolution and recrystallization, purification, separation, pumping, and transport therebetween.

Equipment items which are particularly suitable for fabrication from the specific alloy in accordance with this invention include, for instance, the hydrocyclone described in U.S. Pat. No. 3,598,818, pumps, piping components, and the like. It should be understood that for the process to be within the scope of this invention it is not necessary that all of the equipment, or all parts thereof, be fabricated of the particular ferritic austenitic alloy, provided that at least a part of the surface of some of the equipment which comes into contact with the solution or suspension of melamine is fabricated therefrom.

DETAILED DESCRIPTION OF THE INVENTION

The invention will now be illucidated with the following examples.

With the aid of gaseous ammonia, 22 tons of urea per hour were atomized and sprayed into a bed of silica alumina particles fluidized with ammonia within a melamine synthesis reactor. This fluidized bed was maintained at a temperature of 390° C. by means of heating coils. The gaseous melamine-containing gas therein formed was removed from the melamine reactor and quenched or cooled with a recircilating mother liquor to form a suspension containing solid melamine. By subsequent processing such as described in U.S. Pat. No. 3,598,818, approximately 7300 kg of melamine powder was obtained.

Several items of processing equipment, including column parts, piping components, and pumps, were made of a ferritic austenitic stainless steel with the following composition:

25 percent by weight chromium
5.8 percent by weight nickel
2.6 percent by weight molybdenum
1.7 percent by weight copper
0.06 percent by weight carbon
0.3 percent by weight silicon
less than 1.0 percent by weight contaminants, such as manganese, sulphur and phosphorus.

Corrosion of this material in these various equipment components remained acceptable in all cases.

Additionally, exposure plates constructed of a number of different materials were attached in several locations within the melamine processing equipment described above. The composition of these exposure plates is itemized in the following Table 1.

TABLE 1

| | | Composition of Exposure Plates (% wt.) | | | | | |
|---|---|---|---|---|---|---|---|
| material | structure* | Cr | Ni | Mo | Cu | C | Particulars |
| 1 | FA | 25.0 | 5.8 | 2.6 | 1.7 | 0.06 | |
| 2 | A | 17.0 | 13.7 | 4.3 | — | 0.034 | 1.4 Mn; 0.14 N |

TABLE 1-continued

Composition of Exposure Plates (% wt.)

| material | structure* | Cr | Ni | Mo | Cu | C | Particulars |
|---|---|---|---|---|---|---|---|
| 3 | A | 17.3 | 12.7 | 2.7 | — | 0.019 | 1.6 Mn |
| 4 | A | 15.3 | 67.2 | 15 | — | 0.010 | 0.5 Mn |
| 5 | A | 20.0 | 34.4 | 2.5 | 3.3 | 0.032 | 1.68 Mn; 0.86 Nb |
| 6 | FA | 25 | 6 | 2 | — | 0.03 | |
| 7 | A | 16.04 | rest | 14.91 | — | 0.02 | |
| 8 | A | 17.0 | 11.70 | 2.31 | — | 0.015 | 1.49 Mn |
| 9 | A | 27 | 31 | 3.5 | 1.5 | 0.02 | 1.8 Mn |
| 10 | A | 25.1 | 22.2 | 2.08 | — | 0.015 | 1.68 Mn; 0.148 N |
| 11 | A | 17.4 | 11.80 | 1.76 | — | 0.048 | 1.76 Mn |
| 12 | A | 17.40 | 13.40 | 4.30 | — | 0.029 | 1.30 Mn; 0.125 N |
| 13 | A | 21.9 | 23.8 | 4.41 | 1.30 | 0.015 | 1.56 Mn |

*A = austenitic
FA = ferritic austenitic

The balance of the components contained in these materials was iron and contaminants, except for materials numbers 4 and 7 which were Ni-alloys which were relatively much more expensive than the stainless steels, and were included for purposes of comparison.

The following Table 2 shows the performance of materials 1 through 5 which were placed in the equipment in which ammonia and carbon dioxide escaped from the quenching of melamine with mother liquor are condensed from the gas phase. These conditions are so severe that this equipment is usually fabricated from titanium, and the usual austenitic Cr—Ni-steel, such as material No 3 cannot be used.

TABLE 2

Exposure Time: 13½ Months

| No. | Test Material | Structure* | Corrosion Rate mm/Year |
|---|---|---|---|
| 1 | X5CrNiMoCu 25-5-3-2 | FA | 0.09 |
| 2 | X4CrNiMoN 17-13-5 | A | 0.9 |
| 3 | X3CrNiMo 17-12-2 | A | 1.5 |
| 4 | X1NiCrMo 60-15-15 | A | 0.22 |
| 5 | X5NiCrCuMoNb 35-20-3-2 | A | ≧2 |

*A = austenitic, FA = ferritic austenitic

Table 3 provides the results of additional exposure plates 6 through 8, which were attached in the same equipment as exposure plates 1 through 5 above, but their exposure time was shorter.

TABLE 3

Exposure Time: 132 Days

| No. | Test Material | Structure | Corrosion Rate mm/Year |
|---|---|---|---|
| 6 | X3CrNiMoN 25-5-2 | FA | 0.01 |
| 7 | X0NiCrMo 60-15-15 | A | 0.16 |
| 8 | X3CrNiMo 17-12-2 | A | 1.26 |

From Tables 2 and 3, it can be clearly seen that the use of the ferritic austenitic stainless steel alloy of the present invention (exposure plates 1 and 6) provide far greater corrosion resistance than the other materials tested, and may be acceptably substituted for titanium, which is far more difficult to fabricate and expensive, in those parts of equipment which must withstand very severe conditions.

Table 4 itemizes the results obtained from exposure plates that were attached in condensing equipment fabricated from Hastelloy C 276 (material No. 7), in which ammonia, carbon dioxide, and water vapor were condensed from a gas phase.

TABLE 4

Exposure Time: Approximately 4 Years

| No. | Test Material | Structure | Corrosion Rate mm/Year |
|---|---|---|---|
| 7 | XoCrNiMo 60-15-15 | A | ≦0.01 |
| 1 | X5CrNiMoCu 25-5-3-2 | FA | ≦0.01 |
| 9 | X2NiCrMoCu 30-27-3-2 | A | 0.06 |
| 10 | X2CrNiMoN 25-22-2 | A | 0.12 |
| 11 | X3CrNiMo 17-12-2 | A | 0.20 |

This Table 4 again clearly shows that the ferritic austenitic stainless steel alloy in accordance with the present invention can successfully be substituted for Ni-alloys, which are expensive and difficult to handle, even in places where the usual Cr—Ni-steels fail.

A number of different exposure plates were attached within the outer periphery of a bend in the discharge line of the discharge pump from the quenching column (prepared from Hastelloy C 276 as above), where the flow velocity of the suspension of melamine particles in the aqueous ammonium carbamate solution was about 3 meters per second. The results of this combined corrosion and errosion on the exposure plates are shown on Table 5.

TABLE 5

Exposure Time: Approximately 2 Years

| No. | Test Material | Structure | Corrosion Rate mm/Year |
|---|---|---|---|
| 7 | XoCrNiMo 60-15-15 | A | 0.1 |
| 1 | X5CrNiMoCu 25-5-3-2 | FA | 0.1 |
| 12 | X4CrNiMoN 17-13-5 | A | 0.25 |
| 9 | X2NiCrMoCu 30-27-3-2 | A | 0.8 |
| 13 | X2NiCrMoCu 25-20-3-2 | A | 0.9 |
| 10 | X2CrNiMoN 25-22-2 | A | 1.0 |
| 11 | X3CrNiMo 17-12-2 | A | 1.5 |

Again, it can clearly be seen that under these corrosion/errosion conditions, the ferritic austenitic alloy in accordance with the present invention (material No. 1) is equally as resistant as the far more expensive and difficult to handle Hastelloy C 276 (material No. 7), and far more resistant than the other stainless steel alloy materials.

What is claimed is:

1. In a method for the preparation of melamine by the conversion of urea and/or thermal decomposition products thereof, wherein the synthesis effluent from the melamine reactor, containing ammonia, carbon dioxide and gaseous melamine, is cooled by means of an aqueous medium thereby forming a corrosive-erosive aqueous solution or suspension containing ammonium carbamate and melamine, which aqueous solution or suspension is further processed to remove solid product melamine therefrom, the improvement wherein, in order to substantially resist the corrosive-erosive effect of said solution or suspension, at least a portion of the equipment surfaces exposed to said solution or suspension during processing is fabricated from a stainless steel with a ferritic austenitic duplex structure containing, by weight, from about 20 to 30 percent chromium, 1 to 10 percent nickel, from 0 to about 10 percent manganese, such that the sum of the nickel plus one-half of the manganese content is within the range of between 4 and 10 percent, 1 to 5 percent molybdenum, 0 to 3 percent copper, and not more than 0.1 percent carbon, the remainder being iron and not more than about 5 percent by weight impurities and other additives, relative to the total weight of said stainless steel, and wherein said processing is carried out in the absence of passivating oxygen.

2. The method of claim 1 wherein said stainless steel contains from about 1 to 2.5 percent by weight copper.

3. The method of claim 1 wherein said stainless steel contains additives in an amount of from about 0.2 to 1.0 percent by weight selected from the group consisting of titanium, niobium, and a combination of niobium and tantalum.

* * * * *